United States Patent [19]

Willis

[11] Patent Number: 4,633,063
[45] Date of Patent: Dec. 30, 1986

[54] VENTED HEATING ELEMENT FOR STERILE CUTTING AND WELDING TOGETHER OF THERMOPLASTIC TUBES

[75] Inventor: Frank M. Willis, Wenonah, N.J.

[73] Assignee: E. I. Du Pont de Nemours and Company, Wilmington, Del.

[21] Appl. No.: 686,755

[22] Filed: Dec. 27, 1984

[51] Int. Cl.⁴ .................. B29C 27/06; H05B 3/10; B26D 7/10
[52] U.S. Cl. ........................... 219/243; 30/140; 83/171; 156/304.6; 156/515; 156/518; 156/583.1; 219/221; 219/227; 219/544; 338/248; 338/250; 338/251; 338/255
[58] Field of Search ............... 219/221, 227, 229, 230, 219/540, 544, 534; 156/304.2, 304.6, 583.1, 583.2, 503, 515, 518; 30/140; 83/170, 171; 338/274, 254–257, 243–251

[56] References Cited

U.S. PATENT DOCUMENTS 4,210,800 7/1980 Van Bokestal et al. ......... 219/540 X
4,501,951 2/1985 Benin et al. ..................... 219/227 X

FOREIGN PATENT DOCUMENTS 2531529 2/1977 Fed. Rep. of Germany ...... 338/274
752818 7/1980 U.S.S.R. ............................ 338/274

Primary Examiner—Anthony Bartis

[57] ABSTRACT

A heating element for sterilely melt-cutting and welding together a pair of thermoplastic tubes transversely of the axis of the tubes includes an outer folded metal sheet, such as copper, aluminum, silver or gold, an electric resistance heating element of stainless steel or the like disposed inside the fold of the sheet and a dielectric adhesive disposed between the inner surfaces of the sheet and the resistor to insulate the resistor from the sheet and bond the structure together. The folded edge of the sheet forms the melting edge of the heating element. Vent channels within the adhesive and along at least one unfolded edge of the metal sheet are provided to vent entrapped gas from the element during heating. The channels have a predetermined cross-sectional area and length such that the pressure driven flow of entrapped gas passing through the channels is greater than the pressure-generating vaporization rate of the trapped gases to prevent the entrapped gas from reaching pillowing pressure within the heating element.

19 Claims, 5 Drawing Figures

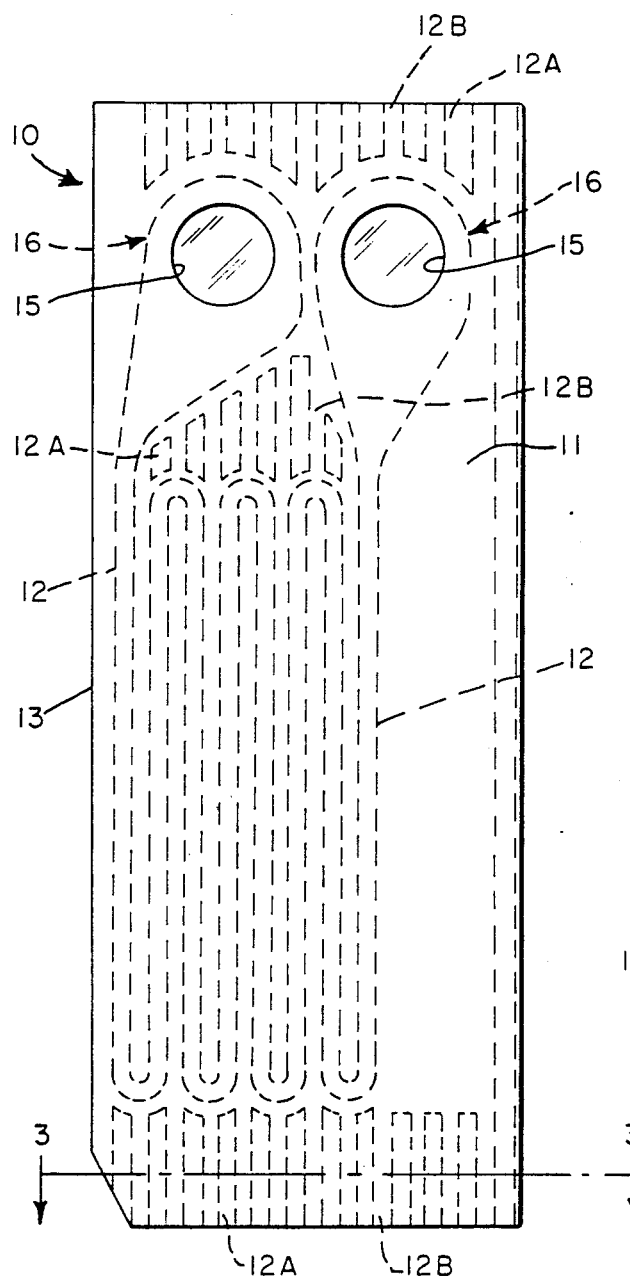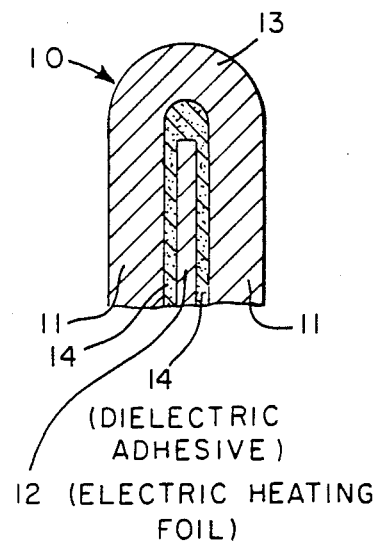

VENTED HEATING ELEMENT FOR STERILE CUTTING AND WELDING TOGETHER OF THERMOPLASTIC TUBES

BACKGROUND OF THE INVENTION

This invention concerns an improved printed circuit heating element. The heating element is useful for the sterile welding of first and second thermoplastic tubes together transversely of the axis of each tube.

This invention represents an improvement in the heating element disclosed in U.S. Pat. No. 4,501,951. The heating element there disclosed was, in turn, an improvement over the heating element disclosed in U.S. Pat. No. 4,369,779. The heating element of U.S. Pat. No. 4,501,951 comprises an outer layer which is a folded sheet of metal; a resistor disposed inside said folded sheet of metal; a layer of dielectric adhesive between the inner surfaces of said folded sheet of metal and said resistor thereby electrically insulating the resistor from the folded sheet and bonding the resulting structure together; said resistor having exposed terminals for reception of electrical current and the folded edge of said metal sheet being the melting edge of the heating element.

SUMMARY OF THE INVENTION

This invention pertains most broadly to an improved resistance-heatable heating element for welding thermoplastic members together, the element having a metal outer surface and a resistor adapted to receive electrical current disposed within the element, the resistor being electrically insulated from the metal surface, wherein the improvement comprises provision of at least one channel located within the heating element and forming at least one pathway to vent entrapped gas from the inside of the heating element to the atmosphere during heating. Contemplated thermoplastic members that can be joined by the heating element of this invention include tubes, pipes, tapes, rods, filaments and the like, of any shape or size amenable to the temperatures and procedures described herein.

The preferred embodiment of this invention concerns an improvement in a resistance-heatable heating element for sterile welding of first and second thermoplastic tubes together transversely of the axis of each tube, the heating element having:

an outer layer of a folded sheet of metal, the folded edge being the heating edge of the heating element;
a resistor disposed inside said folded sheet of metal, the resistor having terminals for reception of electric current;
dielectric adhesive between the folded sheet of metal and the resistor to electrically insulate the resistor from the folded sheet of metal and bond the resulting structure together;
wherein the improvement comprises:
channels located between the resistor and at least one unfolded edge of the folded sheet of metal for venting entrapped gas from the heating element during heating.

The metal employed as the outer layer will have a thermal conductivity of at least about 173 watts per meter °K. (100 BTU ft/hr ft$^2$°F.) for a 0.10 mm (4 mil) thickness and a tensile yield strength of at least about $34 \times 10^4$ kPa (5000 psi) at a 0.10 mm thickness. Suitable metals include copper, aluminum, silver, gold and alloys of these metals. Preferably, the metal is copper, particularly rolled, annealed copper.

The resistor can have a positive, negative or zero thermal coefficient of resistance. A positive thermal coefficient (ptc) of resistance is preferred. Contemplated resistor materials include stainless steel and Nichrome having about 15% chromium by weight. The resistor can be made from a serpentine piece of wire, a stamped foil, or an etched foil. Preferably, the resistor is an etched foil of stainless steel, most preferably, type 302 stainless steel.

The dielectric adhesive should have a dielectric strength sufficient to insulate against a potential of about 24 volts direct current at about 260° C. (500° F.). The adhesive should also display adequate peel strength at about 260° C. to resist delamination of the heating element. A peel strength of at least about 1 lb/inch at 20° C. is sufficient for this purpose. The dielectric adhesive should be relatively resistant to melting and electrical breakdown at temperatures of about 260° to 316° C. (500° to 600° F.) for about 15 to 20 seconds. Suitable adhesives include acrylic adhesives, epoxies, and room temperature vulcanizing silicones. Epoxy and acrylic adhesives are preferred with acrylic adhesives being most preferred (e.g., Pyralux ® acrylic adhesives made by E. I. du Pont de Nemours and Company).

The improved heating element of this invention is contemplated for use in the apparatus disclosed in U.S. Pat. No. 4,369,779. The disclosed apparatus forms a sterile connection between two thermoplastic tubes and comprises a heatable cutting means, a pair of mounting blocks adapted to receive and hold the two tubes, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks and said cutting means while urging said blocks together. The heating element of this invention is also adapted to serve as the cutting means in any sterile connection apparatus similar to that described in U.S. Pat. No. 4,369,779.

The channels between the resistor and at least one of the unfolded edges of the folded metal outer layer form pathways for gases that are occasionally generated during heating of the heating element. There are several ways to design the channels which will be described in more detail hereafter. Typically, addition strips of stainless foil are provided during etching of the resistor element. These boundary strips are arranged so that they direct the flow of any gases that are formed out of the heating element (wafer). The strips are close enough together so the folded outer layer does not deform between the strips and block the channels during final lamination. Without these channels, gases that are sometimes generated during resistance-heating are trapped to generate pressures in excess of 50 psi. These excessive pressures could cause the condition known as "pillowing" to occur in the absence of vent channels. Pillowing is responsible for poor heat transfer and an excessively thick (pillowed) heating element. Use of a pillowed heating element could lead to relatively low-strength, potentially nonsterile welds.

Although the source of the gases is not known for certain, it is believed that they are formed from water or solvent trapped in open passages between the resistor strips of the heating element during its fabrication. Provision of vents eliminates the difficulties and expense involved in diagnosing the source of the gases and altering the manufacturing process to eliminate them.

BRIEF DESCRIPTION OF THE DRAWINGS

FIG. 1 is a fragmentary sectional view of a heating element showing the fragment encompassing the fold but not showing the gas vent channels.

FIG. 2 is a plan view of a heating element of this invention showing one arrangement of gas vent channels.

DETAILS OF THE INVENTION

Figure 3:
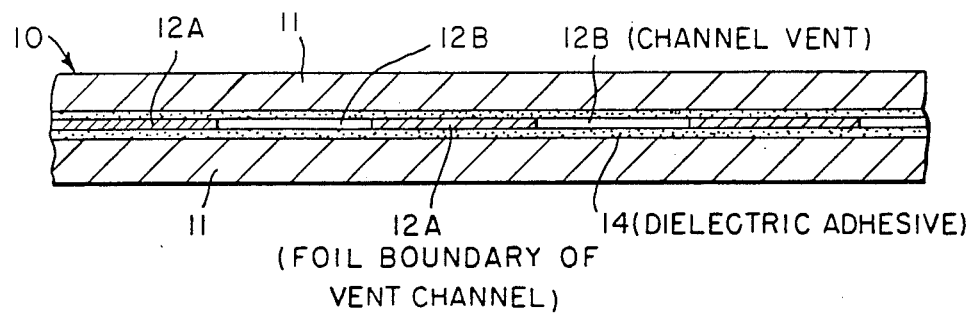
FIG. 3 is an enlarged view taken along line 3—3 of FIG. 2 showing a cross-sectional fragment of a heating element.

Referring now to FIG. 1, heating element 10 has a folded sheet of metal such as copper 11 as the outer layer. Disposed within the fold 13 of the sheet 11 is a resistor 12, typically etched stainless steel foil. Also, disposed within fold 13 adjacent to the inner surfaces of sheet 11 and surrounding the resistor on both sides and one edge is dielectric adhesive layer 14, typically acrylic adhesive. The folded edge of the outer layer of the heating element serves as its cutting surface.

Referring now to FIG. 2, heating element 10 is shown with resistor 12. Openings 15 are provided on one side of folded sheet 11, thereby exposing terminals 16 of resistor 12. Folded sheet 11 can be a single sheet or can comprise 2 or 3 sheets functioning as a single sheet. For instance, when two sheets are used, one can be folded with a J-shape and the other forms the other side by being mechanically crimped to the J-shaped sheet. When three sheets are used, one sheet forms the curve or fold 13 and the other two are mechanically crimped thereto to form the sides. Other modes of having the sheets cooperate as one will be readily apparent.

FIGS. 2 and 3 depict a typical arrangement of venting channels 12B and channel boundaries 12A. The latter are typically made of stainless steel foil etched in a pattern to complement the pattern of resistor 12. Other patterns are possible as would be obvious to one skilled in the art. For instance, some or all of boundaries 12A and channels 12B could be disposed to one or two of the other unfolded sides of the heating element. The only requirement of concern is a practical one that there be enough channels to adequately serve the function of conducting entrapped gases away from the inside of the heating element before pillowing occurs. The channel boundaries can be made of material other than that used for the resistor so long as the material does not interfere with the function of the resistor and so long as it possesses the structural integrity to continue to define channels 12B after the laminating process. In addition to metallic channel boundaries, dielectric adhesive is also contemplated for this purpose. Dielectric adhesive will be employed in such a manner that vent channels will remain after lamination. An alternative way to form channel vents is to use temporary inserts as the "channel boundaries". These temporary boundaries can be removed after lamination to form open vent channels. This procedure involves the additional step of removing the inserts and hence is not the preferred method of vent formation.

There is a practical limit to the cross-section of the channel. If the channels are unduly wide, they may be sealed off during the pressure lamination process by the outer layer of metal 11 or by 11 together with 14. In that event, the channels may disappear or become unduly constricted so that the entrapped gases will be unable to escape without causing the undesired pillowing phenomenon. If the channels are too narrow they may not provide adequate exit pathways to forestall pillowing.

Figure 5:
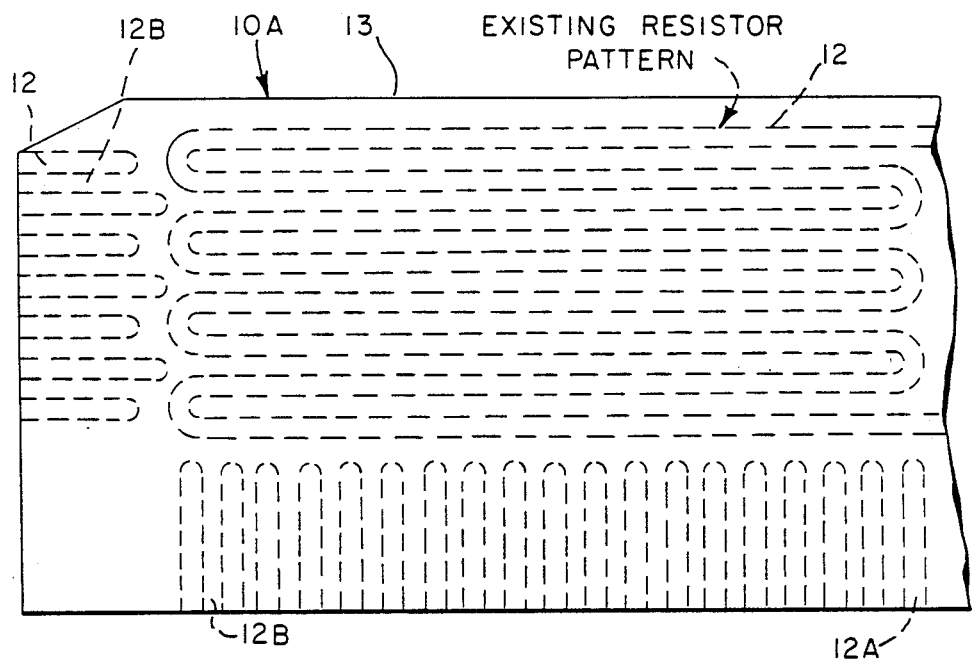
FIG. 5 is a plan view of a fragment of the heating element of this invention showing an alternative arrangement of gas vent channels.

When the vents are properly sized (cross-sectional area and length), the flow rate through them will be such that, before the pillowing pressure is reached, the pressure-driven flow rate will have become greater than the pressure-generating vaporization rate of the trapped volatiles. The pillowing pressure can be estimated knowing the peel strength of the lamination and the area the pressure is acting on. The multiple vents shown in FIGS. 2 and 5 are typically about 20 mils wide, 1 mil high and 150 to 200 mils long. Channels of these dimensions have been found to reliably vent the gases generated in the heating element during use.

The channel/channel boundary arrangement can be configured in any convenient way so long as the channels maintain their integrity after the lamination process and so long as they provide sufficient ventways for the entrapped gas. Typically, the channels can be disposed generally parallel to the folded edge of the outer layer of metal; see FIG. 2 for one such configuration of channels. Alternatively, some or all of the channels can be disposed transversely of the folded edge of the outer layer (see FIG. 5) or there can be any other disposition of channels consistent with the functional criteria that have been defined for them.

Folded sheet 11 is made from a metal having good thermal conductivity to distribute heat evenly along the surface thereby avoiding hot spots. It is known that heat flow due to conductance is proportional to thermal conductivity, area perpendicular to heat flow, and thermal gradient. Therefore, a thicker sheet, with higher cross-sectional area, could provide the same heat flow (for a given gradient) with a metal of lower thermal conductivity. Thus, if sheet 11 is thicker than 0.10 mm, a thermal conductivity proportionately less than 173 watts/m °K. is suitable. Good thermal conductivity also imparts to the heating element the ability to maintain a satisfactory surface temperature during use, i.e., when melting through two tubes to be joined.

The metal of the outer layer must also meet the recited requirements for tensile yield strength to withstand the working load to which the heating element is subjected; for example, at least $34 \times 10^4$ kPa (5000 psi) at 0.10 mm thickness. A thicker sheet, with higher cross-sectional area, could resist the same working load with a metal of lower strength. Thus, if sheet 11 is thicker than 0.10 mm, a tensile yield strength proportionately less than $34 \times 10^4$ kPa would be suitable to resist the working load during use. The metal also has to be sufficiently malleable so that the sheet can be folded without cracking or splitting. The metal must be compatible with any fluid contained in bags to which the tubing being cut is connected. The metal should not, at the temperature of use, react to give off products deleterious to the recipient of the fluid contained in the bag.

Heating element 10 can have a thickness of about 0.13 mm (5 mil) to 0.76 mm (30 mil), preferably about 0.25 mm (10 mil) to 0.36 mm (14 mil). Most preferably, the heating element has a thickness of about 0.30 mm (12 mil). In a preferred embodiment of the invention, the adhesive layer and the resistor are each 0.025 mm (1 mil) thick. Preferably, the outer layer is about 0.11 mm (4.2 mil) in thickness.

When using an acrylic adhesive, the heating element of the invention is prepared by first carefully cleaning the resistor and one side of the sheet of metal using techniques well known in the art. A sheet of adhesive is placed on top of the cleaned surface of the sheet of metal and the resistor material is then placed on top of the adhesive layer. The resulting composite is laminated by placing it in a press and subjecting it to a temperature of about 188° C. (370° F.) and a pressure of about 827 kPa (120 psi) for about 45 minutes and then cooling for about 20 minutes under the same pressure. The laminate is then resist-coated using methods well known in the art, exposed, developed, etched, stripped, dried and punched in the usual way to provide the etched resistor 12. The sheet of metal is folded and the resulting folded unit is laminated by placing it in a press at about 188° C. (370° F.) and about 117 kPa (17 psi) of pressure for about 45 minutes. The resulting element is cooled for about 20 minutes under the same pressure to give the heating element of the invention.

Figure 4:
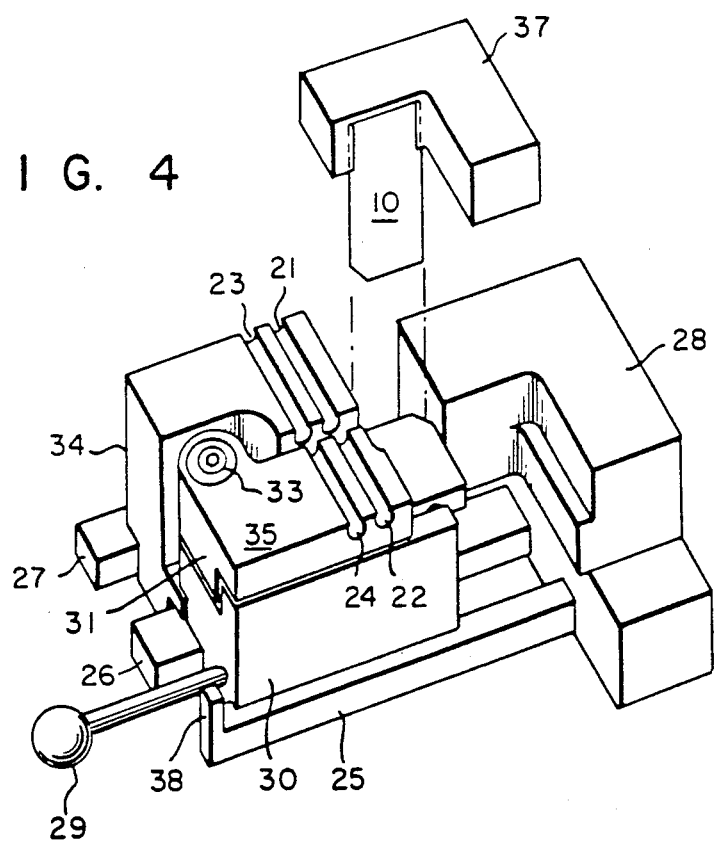
FIG. 4 is a perspective view of a sterile connection apparatus containing the heating element depicted in FIG. 2.

FIG. 4 shows a sterile connection apparatus according to U.S. Pat. No. 4,369,779. In operating the device, the operator inserts the ends of the tubes in slots 21-22 and 23-24 of mounting blocks 34 and 35. Heating element 10 can be mounted to block 37, which in this embodiment serves as a holder rather than a heater, and activated by conventional means. Heating element 10 and block 37 are lowered so that heating element 10 is positioned between stopblock 28 and mounting blocks 34 and 35 in alignment with the space between said mounting blocks. This positioning is effected by having the mounting blocks and block 37 fixedly arranged in a suitable housing (not shown).

The heating element is activated. The operator pushes handle 29 which moves blocks 30 and 34 together on slides 25, 26 and 27, thereby moving the tubes across heating element 10. Block 34 strikes stopblock 28 first thereby causing the two blocks to become sufficiently disengaged so that block 35 moves on to stop against stopblock 28. This further movement by block 35 aligns slots 21 and 24 as the cut tube ends remain sealed by molten polymer against heating element 10. The operator immediately withdraws handle 29 to move block 35 which is connected to handle 29 and, by friction between the blocks through pressure exerted by a pin (not shown) on block 35, block 34 also. The blocks and the tube ends to be joined move back away from heating element 10. As the corner of block 35 leaves the edge of block 28, a spring (not shown) urges part 31 of block 35 to rotate slightly about bolt 33 toward block 34 so that slight compression is urged on the tube ends being joined as they slide off the edge of the heating element. Stop 38 on slide 25 terminates the motion of the blocks and handle. When using the heating element of the invention as the cutting means in the aforesaid sterile docking apparatus, a temperature of about 271° C. (520° F.) is preferably utilized.

I claim:

1. In a heating element for sterile welding of first and second thermoplastic tubes together transversely of the axis of each tube, the heating element having:

an outer layer formed of a folded sheet of metal, the folded edge being the heating edge of the heating element;

a resistor disposed inside said folded sheet of metal, the resistor having terminals for reception of electric current;

dielectric adhesive between the folded sheet of metal and the resistor to electrically insulate the resistor from the folded sheet of metal and bond the resulting structure together;

the improvement comprising:

channels located within the adhesive between the resistor and the sheet of metal and along at least one unfolded edge of the folded sheet of metal for venting entrapped gas from the heating element during heating, the channels having a predetermined cross-sectional area and a predetermined length so that the pressure driven flow of entrapped gas passing through the channels is greater than the pressure-generating vaporization rate of the trapped gases within the heating element to prevent the entrapped gas from reaching a pillowing pressure within the heating element.

2. A heating element according to claim 1 wherein the resistor has a positive thermal coefficient of resistance and a thickness of about 0.13 mm to 0.76 mm.

3. A heating element according to claim 2 wherein the metal of the folded sheet is selected from the group consisting of copper, aluminum, silver, gold and alloys thereof.

4. A heating element according to claim 3 wherein the resistor is an etched foil resistor made of stainless steel or of Nichrome having 15% chromium by weight.

5. A heating element according to claim 4 wherein the adhesive is selected from the group consisting of an epoxy or an acrylic adhesive.

6. A heating element according to claim 5 wherein the adhesive is an acrylic adhesive.

7. A heating element according to claim 6 wherein the outer layer is made of copper.

8. A heating element according to claim 7 wherein the etched foil resistor is made of stainless steel.

9. A heating element according to claim 1 wherein the vent channels are disposed generally parallel to the folded edge of the outer layer of metal.

10. A heating element according to claim 1 wherein at least some of the vent channels are disposed transversely of the folded edge of the outer layer of metal.

11. In an apparatus for forming a sterile connection between two thermoplastic tubes which comprises a heatable cutting means, a pair of mounting blocks adapted to receive and hold the two tubes, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks together;

the cutting means comprising a heating element having an outer layer formed of a folded sheet of metal, the folded edge being the heating edge of the heating element; a resistor disposed inside said folded sheet of metal, the resistor having terminals for reception of electric current; dielectric adhesive between the folded sheet of metal and the resistor to electrically insulate the resistor from the folded sheet of metal and bond the resulting structure together;

the improvement which comprises:

channels located within the adhesive between the resistor and the sheet of metal and along at least one unfolded edge of the folded sheet of metal for venting entrapped gas from the heating element during heating, the channels having a predetermined cross-sectional area and a predetermined length so that the pressure driven flow of entrapped gas passing through the channels is greater than the pressuregenerating vaporization rate of trapped gas to prevent the entrapped gas from reaching a pillowing pressure within the heating element.

12. An apparatus according to claim 11 wherein the resistor of the heating element has a positive thermal coefficient of resistance and a thickness of about 0.13 mm to 0.76 mm.

13. An apparatus according to claim 12 wherein the metal of the heating element is selected from the group consisting of copper, aluminum, silver, gold and alloys thereof.

14. An apparatus according to claim 13 wherein the resistor of the heating element is an etched foil resistor made of stainless steel or of Nichrome having 15% chromium by weight.

15. An apparatus according to claim 14 wherein the adhesive is selected from the group consisting of an epoxy or an acrylic adhesive.

16. An apparatus according to claim 15 wherein the adhesive is an acrylic adhesive.

17. An apparatus according to claim 16 wherein the outer layer is made of copper and the etched foil resistor is made of stainless steel.

18. An apparatus according to claim 11 wherein the heating element has vent channels disposed generally parallel to the folded edge of the outer layer of metal.

19. An apparatus according to claim 1 wherein the heating element has vent channels disposed transversely of the folded edge of the outer layer of metal.

* * * * *